United States Patent
Shin

(10) Patent No.: US 10,640,050 B1
(45) Date of Patent: May 5, 2020

(54) HOLDING DEVICE FOR MOTOR VEHICLE AIR FRESHENER

(71) Applicant: Fu-Zong Shin, Taipei (TW)

(72) Inventor: Fu-Zong Shin, Taipei (TW)

( * ) Notice: Subject to any disclaimer, the term of this patent is extended or adjusted under 35 U.S.C. 154(b) by 0 days.

(21) Appl. No.: 16/172,871

(22) Filed: Oct. 29, 2018

(51) Int. Cl.
*B60R 7/08* (2006.01)
*B60H 3/00* (2006.01)
*A61L 9/12* (2006.01)
*B60R 11/00* (2006.01)

(52) U.S. Cl.
CPC ...... *B60R 7/08* (2013.01); *A61L 9/12* (2013.01); *B60H 3/0014* (2013.01); *A61L 2209/15* (2013.01); *B60R 2011/0007* (2013.01); *B60R 2011/008* (2013.01); *B60R 2011/0015* (2013.01); *B60R 2011/0021* (2013.01); *B60R 2011/0059* (2013.01); *B60R 2011/0071* (2013.01)

(58) Field of Classification Search
CPC ............ B60R 7/08; B60R 3/0014; B60R 2011/0007; B60R 2011/0015; B60R 2011/0021; B60R 2011/0059; B60R 2011/0071; B60R 2011/008; A61L 9/12; A61L 2209/15; A61L 9/03; A47G 23/0216; A47G 23/0225; A47G 23/02; A47G 23/0208; B60H 3/0014
USPC ........ 211/71.01, 75, 113; 96/222; 248/309.1, 248/315, 311.2, 310, 312, 312.1, 314
See application file for complete search history.

(56) References Cited

U.S. PATENT DOCUMENTS

| | | | | |
|---|---|---|---|---|
| 4,931,224 A | * | 6/1990 | Holzner, Sr. | A61L 9/122 239/57 |
| 5,042,770 A | * | 8/1991 | Louthan | A47K 1/09 248/205.3 |
| RE33,864 E | * | 3/1992 | Steiner | A61L 9/122 239/57 |
| 5,431,885 A | * | 7/1995 | Zlotnik | A61L 9/122 239/60 |
| D361,924 S | * | 9/1995 | Becker | D7/620 |
| 5,813,579 A | * | 9/1998 | Hendrickson | B60N 3/103 224/42.11 |
| 5,842,671 A | * | 12/1998 | Gibbs | A47G 23/0225 248/231.41 |
| 6,045,017 A | * | 4/2000 | Connell | A45F 5/02 224/148.4 |
| 7,650,948 B2 | * | 1/2010 | Rousseau | A62C 13/70 169/23 |
| 8,500,076 B2 | * | 8/2013 | Lai | A47G 23/0225 224/148.5 |

(Continued)

*Primary Examiner* — Jennifer E. Novosad
(74) *Attorney, Agent, or Firm* — Leong C. Lei

(57) ABSTRACT

A holding device for an air freshener includes a hanging member and a base member. The hanging member includes a rack and a belt. The rack includes two separate hooks arranged in parallel with a reinforcing beam in between. The hooks have their front ends extended downward into two columns, and bended perpendicularly forward and joined into a bottom ring. A top ring is perpendicularly welded to the columns above the bottom ring. The belt has a ring and two belt pieces, and each belt piece is extended from the ring and a buckle at an outer end of the belt piece. The base member includes a cup and an L-shaped seat with a planar element and a wall element. The planar element has a central through opening, and the cup is joined to the planar element from below and exposed by the through opening.

3 Claims, 13 Drawing Sheets

(56) References Cited

U.S. PATENT DOCUMENTS

| | | | | |
|---|---|---|---|---|
| 2003/0106977 | A1* | 6/2003 | Alberts | A62C 13/78 |
| | | | | 248/313 |
| 2004/0108429 | A1* | 6/2004 | Field | A62B 25/00 |
| | | | | 248/311.2 |
| 2005/0163670 | A1* | 7/2005 | Alleyne | A61L 9/03 |
| | | | | 422/125 |
| 2005/0236545 | A1* | 10/2005 | Seil | B60R 11/00 |
| | | | | 248/311.2 |
| 2006/0284040 | A1* | 12/2006 | Nixon | A47G 23/0225 |
| | | | | 248/311.2 |
| 2008/0169397 | A1* | 7/2008 | Somuah | B60N 3/102 |
| | | | | 248/311.2 |
| 2010/0200670 | A1* | 8/2010 | Tipton | A61L 9/12 |
| | | | | 239/6 |
| 2011/0070018 | A1* | 3/2011 | Nedelman | B60R 7/08 |
| | | | | 403/24 |
| 2012/0024725 | A1* | 2/2012 | Zabinski | B60R 7/08 |
| | | | | 206/216 |
| 2013/0334269 | A1* | 12/2013 | Cardonna | B60R 7/08 |
| | | | | 224/554 |
| 2016/0022857 | A1* | 1/2016 | Esses | A61L 9/032 |
| | | | | 392/390 |
| 2017/0120182 | A1* | 5/2017 | Kim | B03C 3/017 |
| 2018/0332952 | A1* | 11/2018 | Barca | B60R 11/02 |
| 2018/0361940 | A1* | 12/2018 | Ackeret | B60R 7/043 |
| 2019/0084493 | A1* | 3/2019 | Muiter | B60N 3/101 |
| 2019/0184907 | A1* | 6/2019 | Weintraub | B60R 7/08 |

\* cited by examiner

HOLDING DEVICE FOR MOTOR VEHICLE AIR FRESHENER

BACKGROUND OF THE INVENTION

(a) Technical Field of the Invention

The present invention is generally related to air fresheners, and more particular to a holding device for reliably positioning an air freshener in a motor vehicle.

(b) Description of the Prior Art

Aromatherapy is a type of alternative medicine that uses fragrance to improve a person's health or mood. Its effectiveness is still under debate. However, it is generally accepted believe that aromatic atmosphere may ease worry, anxiety, or nervousness, and may improve emotion management and health.

Traditionally, aromatic compounds are delivered via vapor, and the vaporization is achieved through heating (e.g., using candles, electrical heater), iso-Propyl alcohol, etc. These methods have shortcomings such as fire hazard, aromatic compounds too big, or ozone may be produced that is harmful to environment.

A better approach is to vibrate at high frequency and atomize the aromatic solution to produce negative ions. However, this kind of devices are mostly designed to be used in households or offices. They are not commonly used inside motor vehicle.

As shown in FIGS. 1A and 1B, a conventional air freshener 1 is usually adhered above the dashboard 100 of a vehicle and includes a bottle 11 and a cap 10. The cap 10 has a through opening 10a through which a cotton wick 11a is threaded so that an end of the cotton wick 11a is dipped in an aromatic chemical solution 11b contained in the bottle 11. As mentioned earlier, this kind of air freshener 1 is obsolete as its vapor usually contains benzene, phenol, alcohol, or other chemicals that are harmful to human. After a period of usage, its scent may also become too strong, causing uneasiness and fatigue to the driver.

FIG. 2A shows another conventional air freshener 2 that includes a nozzle 21, a vapor chamber 22, a body 23, a controller 24, and a cigarette lighter plug 25 through which 12V/24V voltage is drawn from a vehicle's battery.

When the air freshener 2 is positioned above the dashboard 100 as shown in FIG. 2B, its smoke may block the driver's view. It may also topple due to bumpy road conditions or sharp turns. The solution housed in the air freshener 2 may be spilt, thereby damaging or affecting some appliances on the vehicle.

When the air freshener 2 is positioned on a central armrest 200 of the vehicle as shown in FIG. 2C, it again would easily topple and spill the contained solution to damage the vehicle's appliances.

As shown in FIGS. 3A to 3C, the air freshener 2 may also be stored in a bag 3 and the bag 3 is fastened to a vehicle seat by a number of belts 31 and ties 32. This teaching does not consume the limited vehicle space, and does not disrupt the vehicle's original storage function. The air freshener 2, as it is tightly tied to the vehicle seat and held reliably on the armrest, would not be toppled due to road or driving conditions. However, the fastening of the belts 31 and ties 32 is difficult and cumbersome.

SUMMARY OF THE INVENTION

The present invention teaches a holding device for an air freshener. The holding device includes a hanging member and a base member. The hanging member allows the air freshener to be hung at appropriate place inside a vehicle, and the base member allows the air freshener, together with the hanging member, to be reliably positioned in a cup holder of the vehicle. The hanging member includes a rack and a belt. The belt fastens the air freshener to the rack, and the rack may be hung at appropriate locations inside the vehicle. The air freshener does not topple and the solution contained inside does not spill and damage appliance of the vehicle due to bumpy road condition and sharp turns. The air freshener therefore may provide an aromatic atmosphere inside the vehicle to ease the driver's worry anxiety, or nervousness, thereby enhancing the safety of the driver and passengers.

The base member includes a cup and an L-shaped seat with a planar element and a wall element. The planar element has a round front edge with an arc-shaped block extended upward and a linear back edge joined to the wall element. The wall element includes two wall pieces placed side by side with a ditch in between. The wall elements have U-shaped ditches inside facing each other. The planar element has a central through opening, and the cup is joined to the planar element from below and exposed by the through opening. As such the air freshener, together with the hanging member and the base member, may be reliably positioned in a cup holder of various apertures and shapes inside the vehicle.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1A:
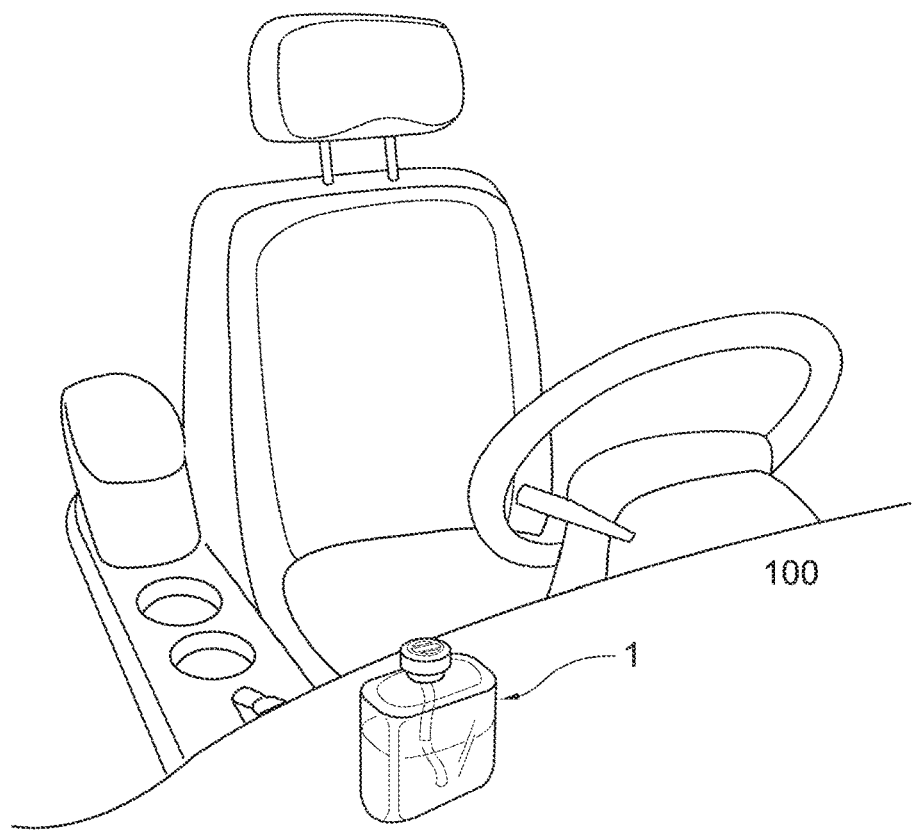
FIG. 1A shows a conventional air freshener applied inside a vehicle.
Figure 1B:
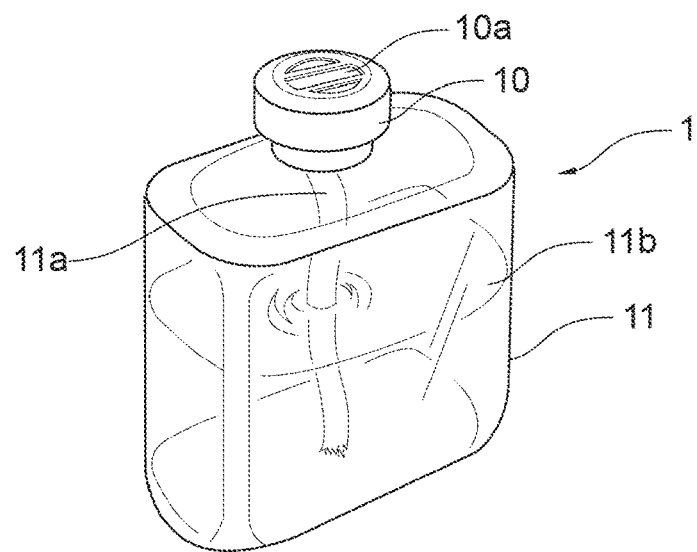
FIG. 1B is a perspective diagram showing the conventional air freshener of FIG. 1.
Figure 2A:
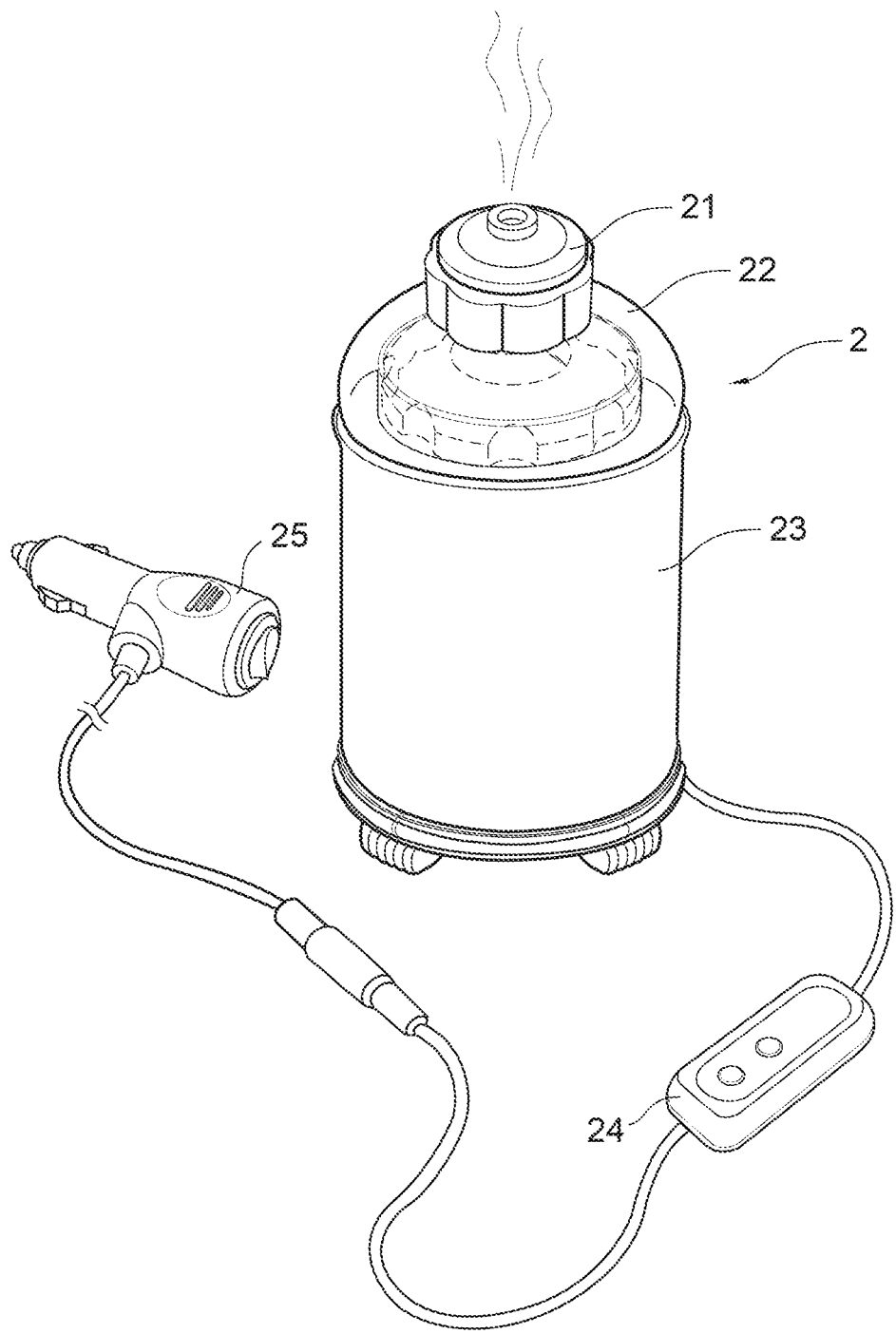
FIG. 2A is a perspective diagram showing another conventional air freshener.
Figure 2B:
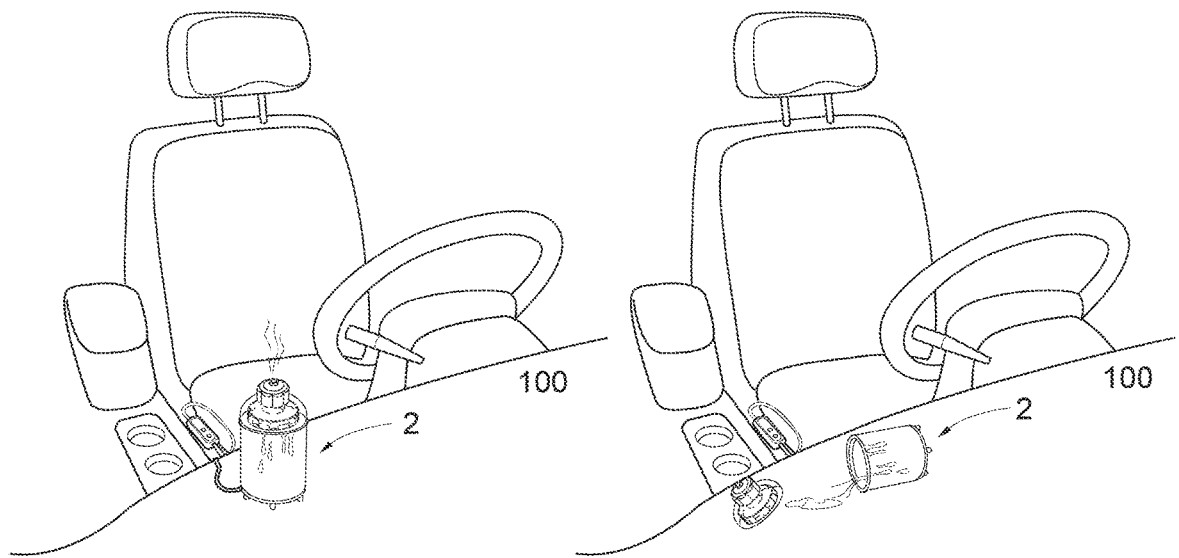
FIGS. 2B and 2C show scenarios of the air freshener of FIG. 2A applied inside a vehicle.
Figure 2C:
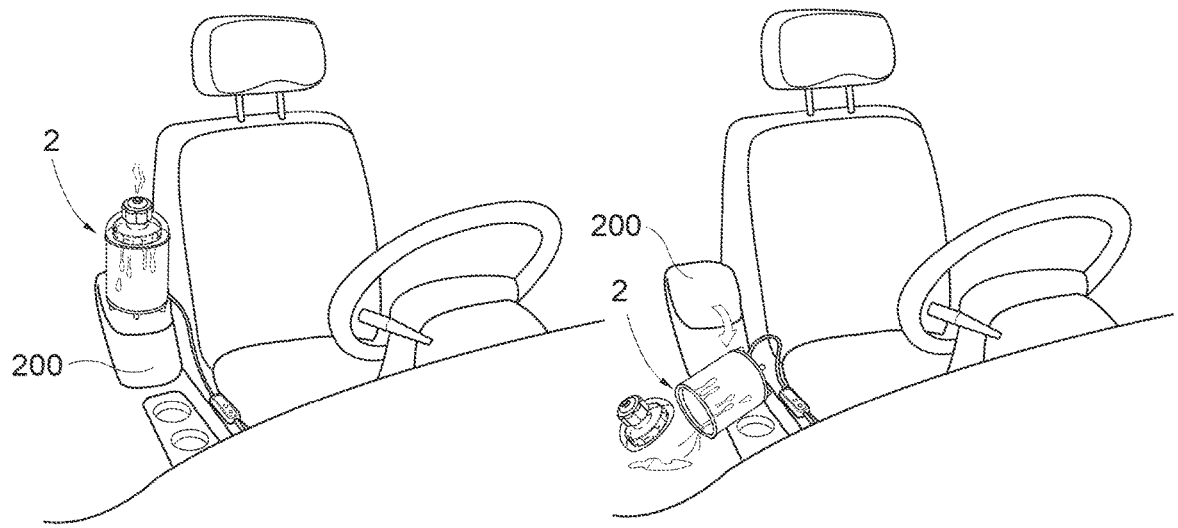
Figure 3A:
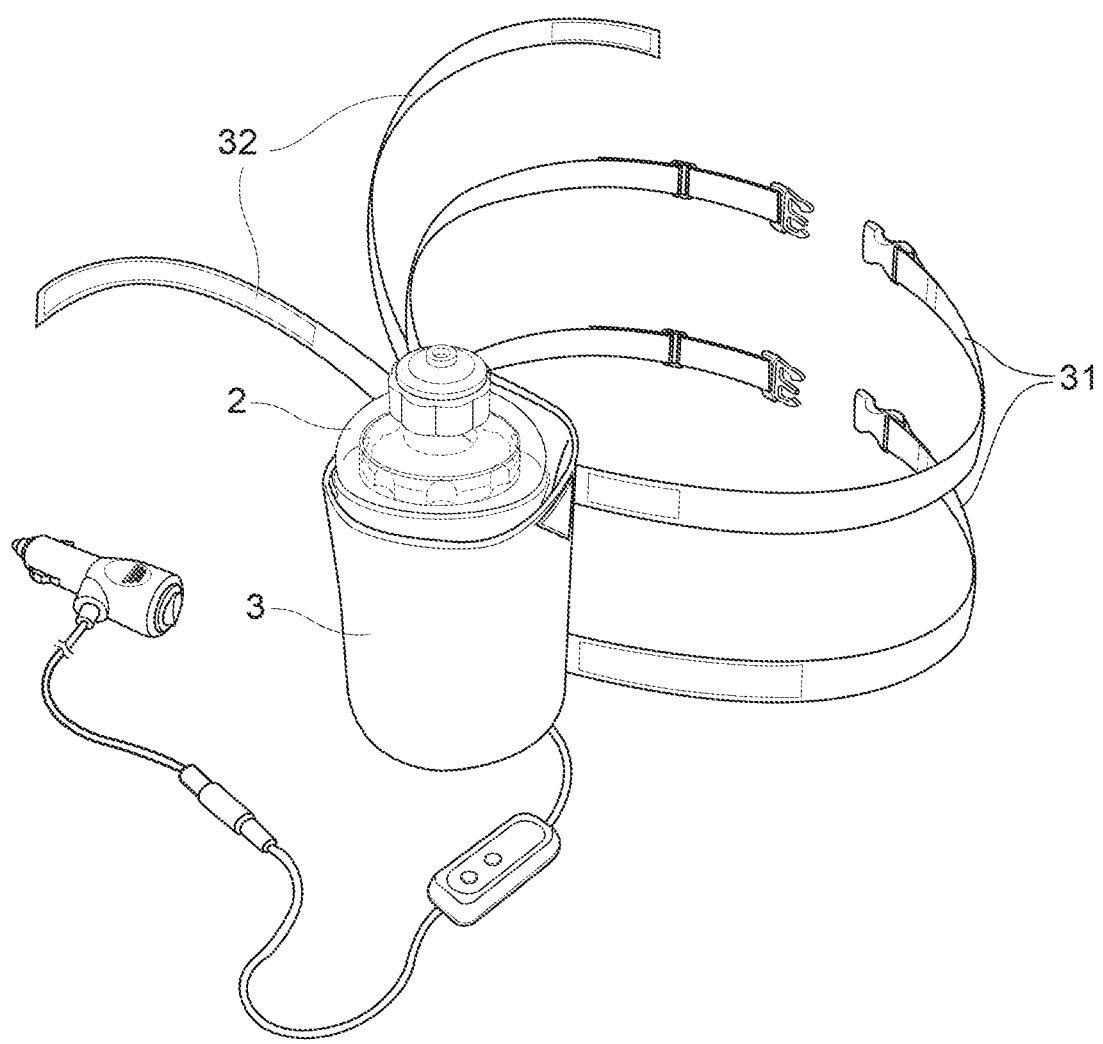
FIGS. 3A to 3C show a conventional means of positioning the air freshener of FIG. 2A inside a vehicle.
Figure 3B:
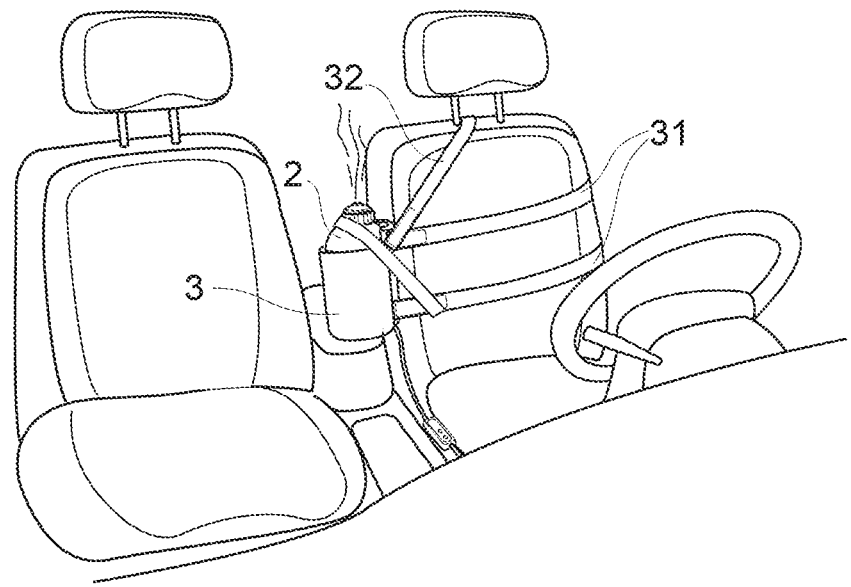
Figure 3C:
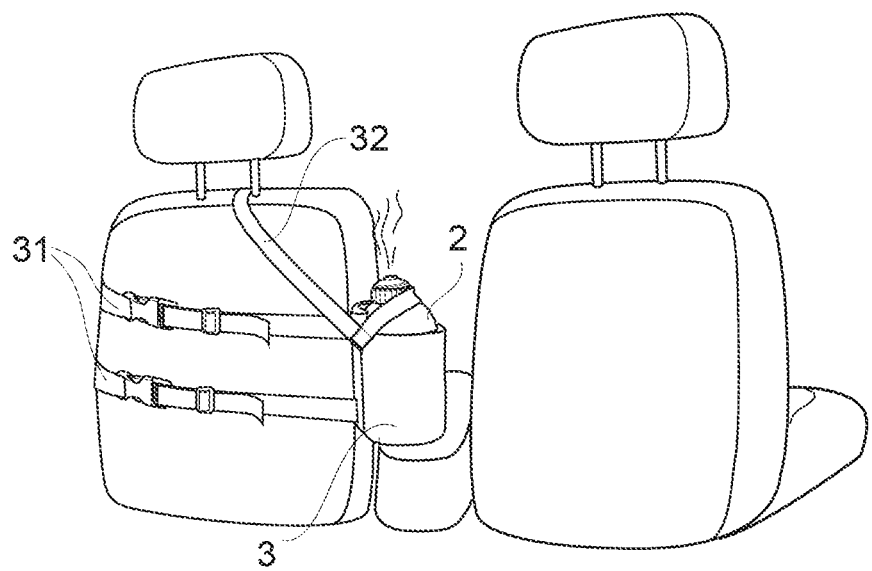
Figure 4:
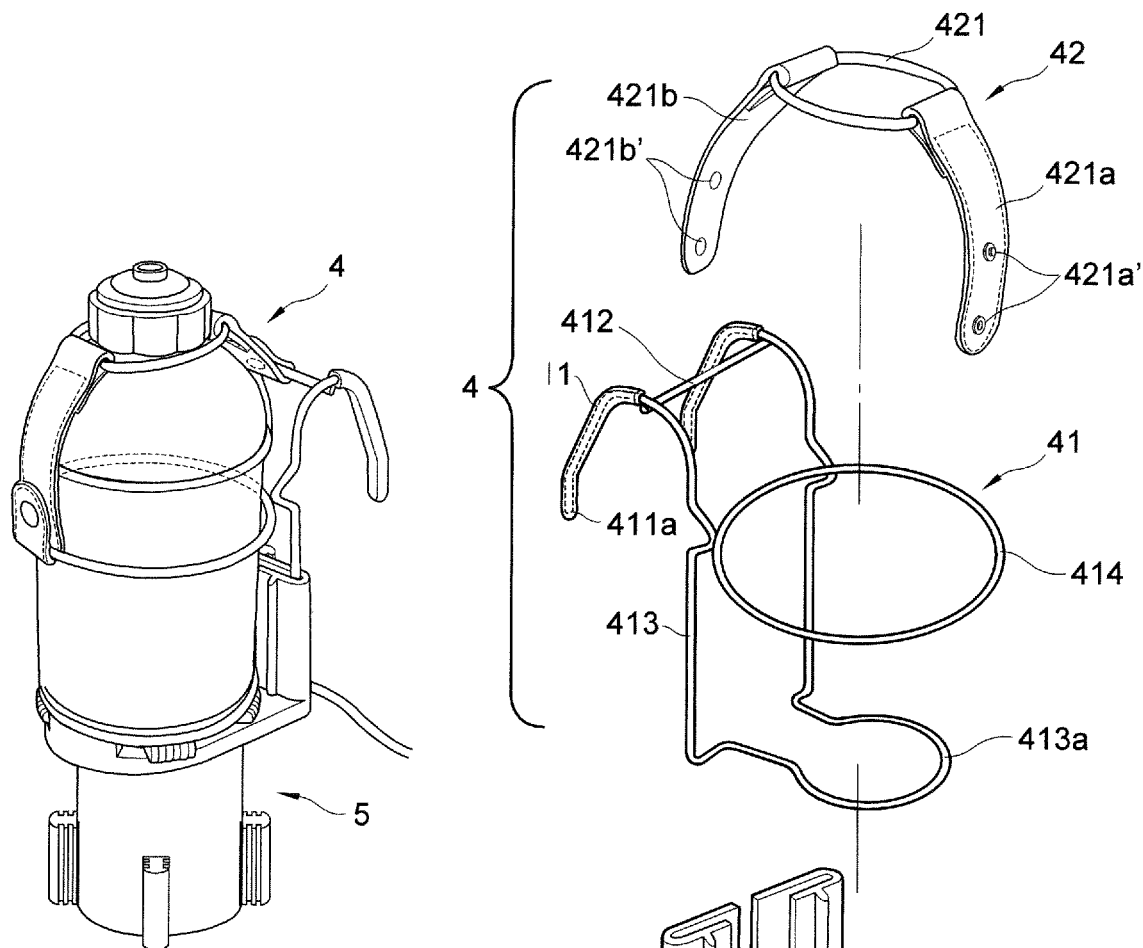
FIG. 4 is a perspective diagram showing a holding device according to an embodiment of the present invention.
Figure 5:
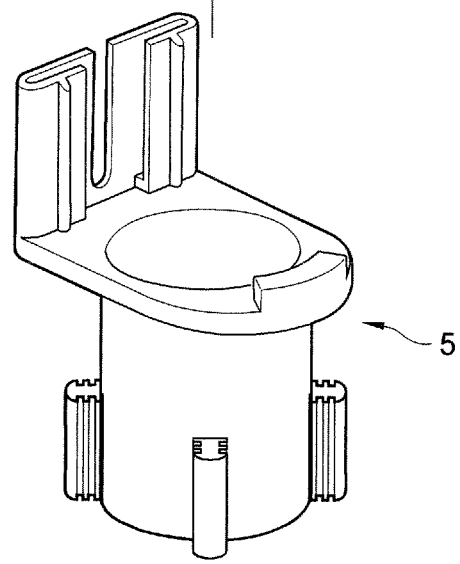
FIG. 5 is a perspective break down diagram showing the holding device of FIG. 4.

As shown in FIGS. 4 and 5, a holding device according to a first embodiment of the present invention includes a hanging member 4 and a base member 5. The hanging member 4 includes a rack 41 and a belt 42. The rack 41 are formed by metallic wires and includes two separate hooks 411 arranged in parallel with a reinforcing beam 412 in between. A back end of each hook 411 is sleeved in a plastic cover 411a. The hooks 411 have their front ends extended downward into two columns 413. The two columns 413 are then bended perpendicularly forward and joined into a bottom ring 413a. A top ring 414 is perpendicularly welded to the columns 413 above the bottom ring 413a. The belt 42 has a ring 421 and two belt pieces 421a and 421b. The belt pieces 421a and 421b are extended from the ring 421 and have buckles 421a' and 421b' at their outer ends.

Figure 6:
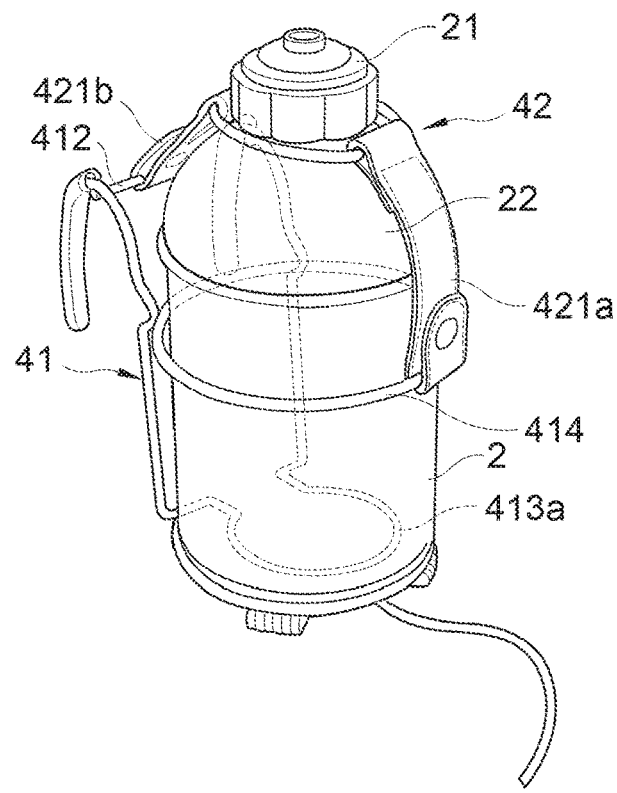
FIG. 6 is a perspective diagram showing an air freshener is mounted on a hanging member of the holding device of FIG. 4.

As shown in FIG. 6 the present embodiment is applied as follows. An air freshener 2 is mounted on the rack 41. The air freshener has its bottom supported by the bottom ring 413a and its body confined by the top ring 414. The air freshener 2 is further locked by the belt 42 by having its ring 421 sleeved over the nozzle 21 on top of the vapor chamber p22 of the air freshener and having the buckle 421a of a belt piece 421 fastened onto the top ring 414 and the buckle 421b of the other belt piece 421 fastened onto the reinforcing beam 412.

Figure 7A:
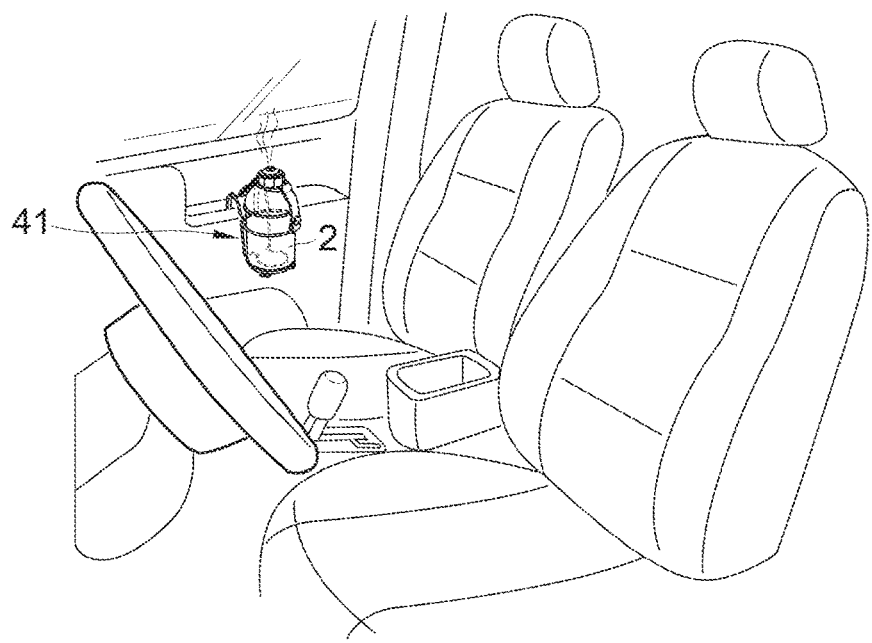
FIGS. 7A to 7C show scenarios of the holding device of FIG. 4 applied inside a vehicle to hold an air freshener.
Figure 7B:
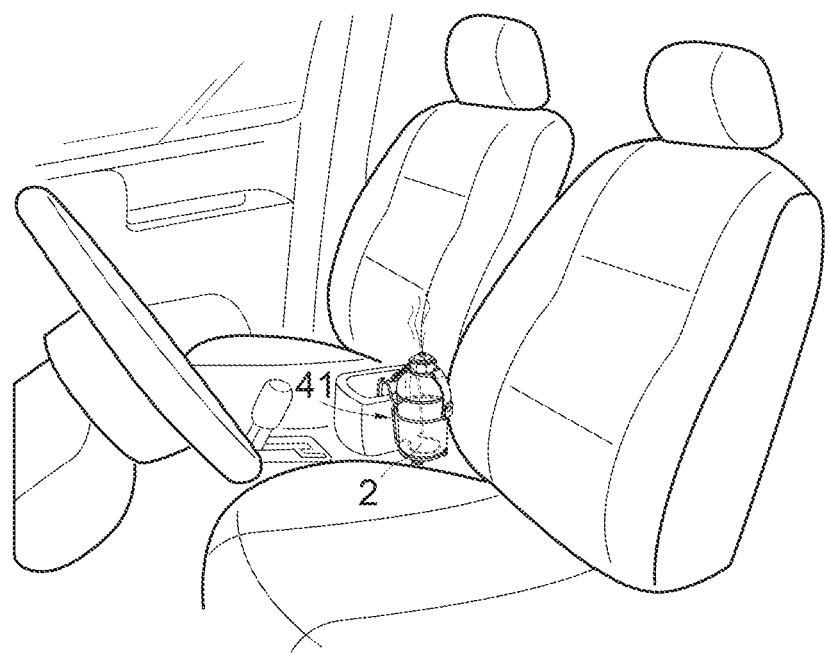
Figure 7C:
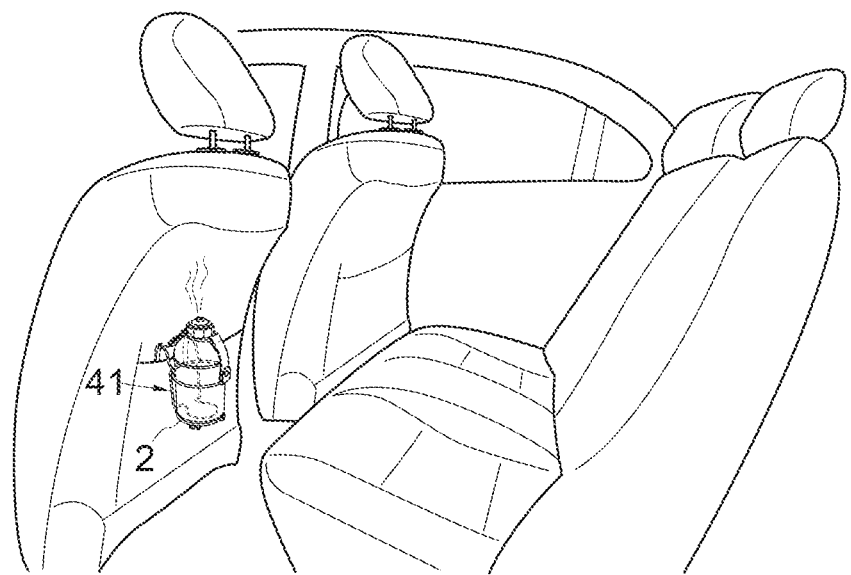

As shown in FIG. 7A, after the air freshener 2 is positioned on the rack 41 as described above, the holding device may be hung on the armrest of a vehicle door. Alternatively, as shown in FIG. 7B, the holding device may be hung to a side of the driver's armrest/storage compartment. As shown in FIG. 7C, the holding device may also be hung to the pocket behind vehicle seat. As illustrated, the holding device may actually be placed anywhere appropriate inside the vehicle.

Figures 8, 9:
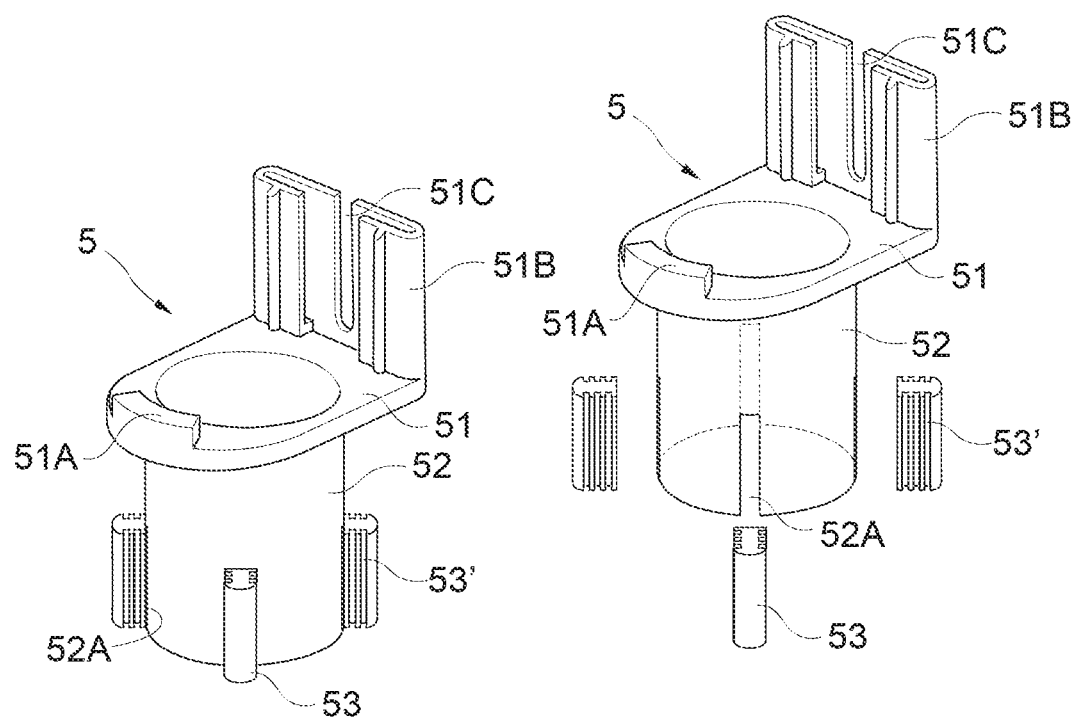
FIG. 8 is a perspective diagram showing a base member of the holding device of FIG. 4.
FIG. 9 is a perspective break down diagram showing the base member of FIG. 8.
Figure 10:
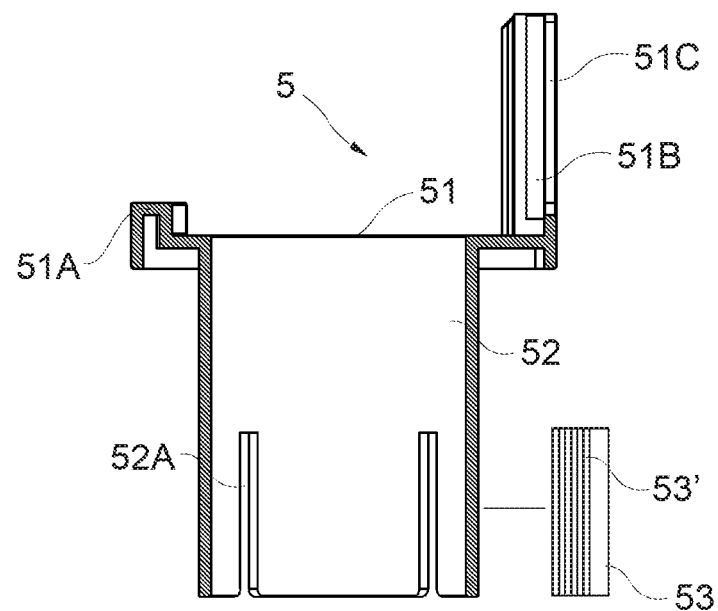
FIG. 10 is a sectional diagram showing the base member of FIG. 8.

As shown in FIGS. 8 to 10, the base member 5 includes a cup 52 and an L-shaped seat 51 with a planar element and a wall element. The planar element has a round front edge with an arc-shaped block 51A extended upward and a linear back edge joined to the wall element. The wall element includes two wall pieces 51B placed side by side with a ditch 51C in between, The wall elements have U-shaped ditches inside facing each other. The planar element has a central through opening and the cup 52 is joined to the planar element from below and exposed by the through opening. Around a lower portion of the circumference of the cup 52, there are four slots 52A configured symmetrically. A silicone block 53 may be plugged into each slot 52A. The silicone blocks 53 has notches along two opposite sides.

Figures 11A, 11B:
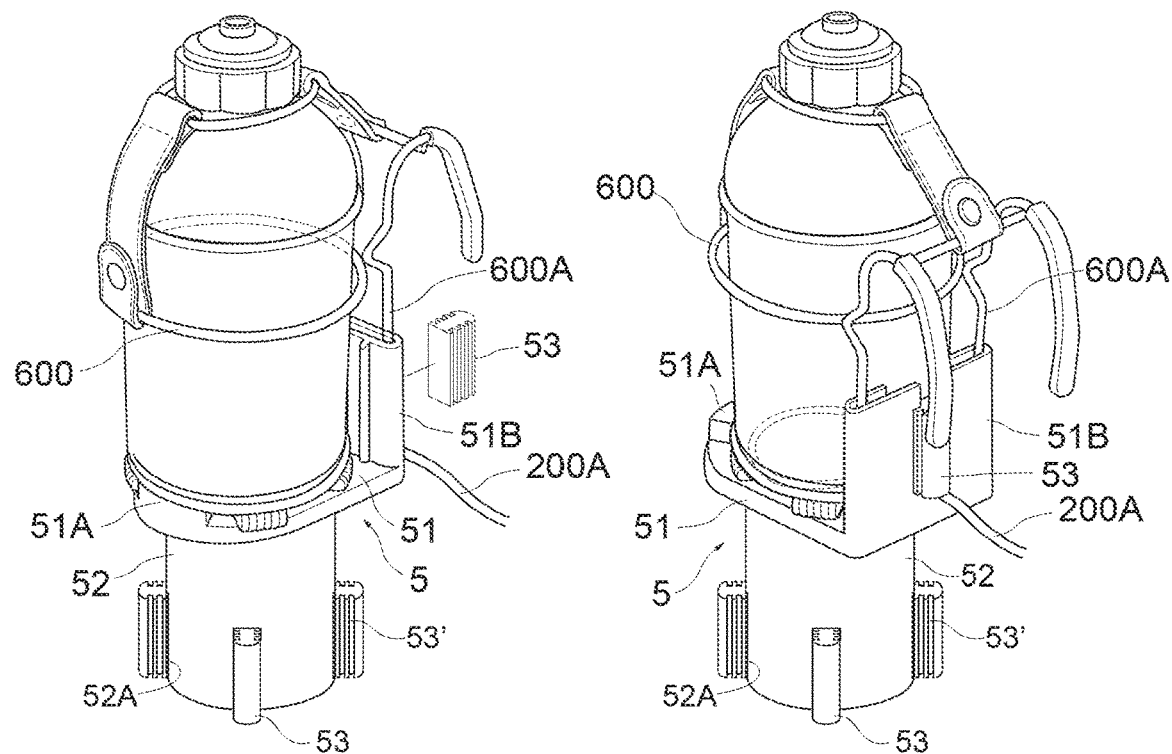
FIG. 11A is a perspective diagram showing an air freshener held by the holding device of FIG. 4.
FIG. 11B is another perspective diagram showing an air freshener held by the holding device of FIG. 4.
Figure 12:
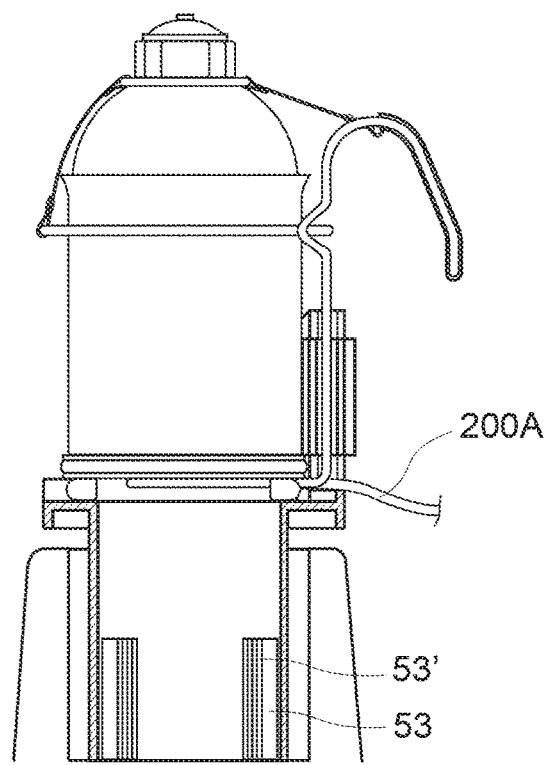
FIG. 12 is a profile diagram showing an air freshener held by the holding device of FIG. 4.

As shown in FIGS. 11A 11B, and 12, after the air freshener 2 is positioned on the rack 41, they are then plugged into the base member 5. The columns 413 are embedded into the U-shaped ditches 51B. The arc-shaped block 51A is in front of and confines the air freshener 2. A power cable 200A of the air freshener may run through the ditch 51C and a silicon block 53 may be inserted into the ditch 51C to confine the power cable 200A and to reliably position the hanging member 4 on the L-shaped seat 51.

Figure 13A:
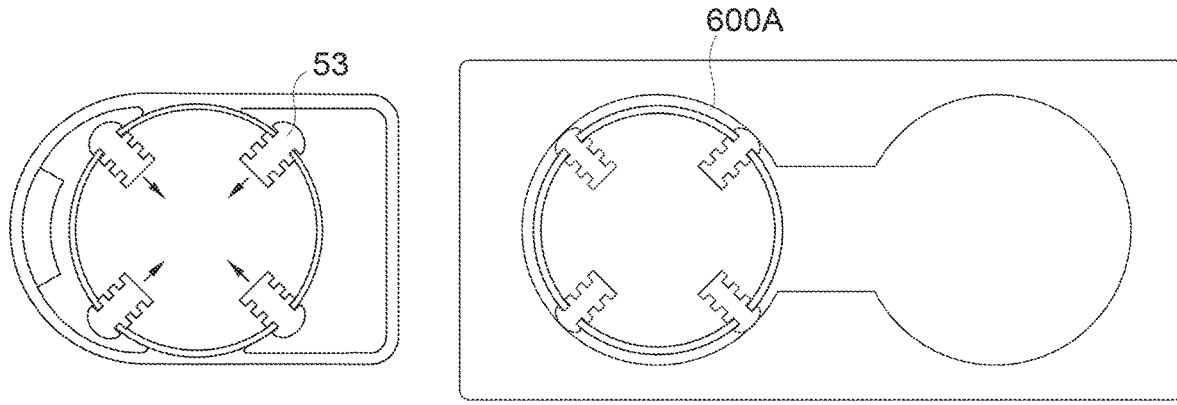
FIGS. 13A to 13C are top-view diagrams showing various adjustments to silicone blocks of the holding device of FIG. 4 so as to fit vehicle cup holders of different aperture and shapes.
Figure 13B:
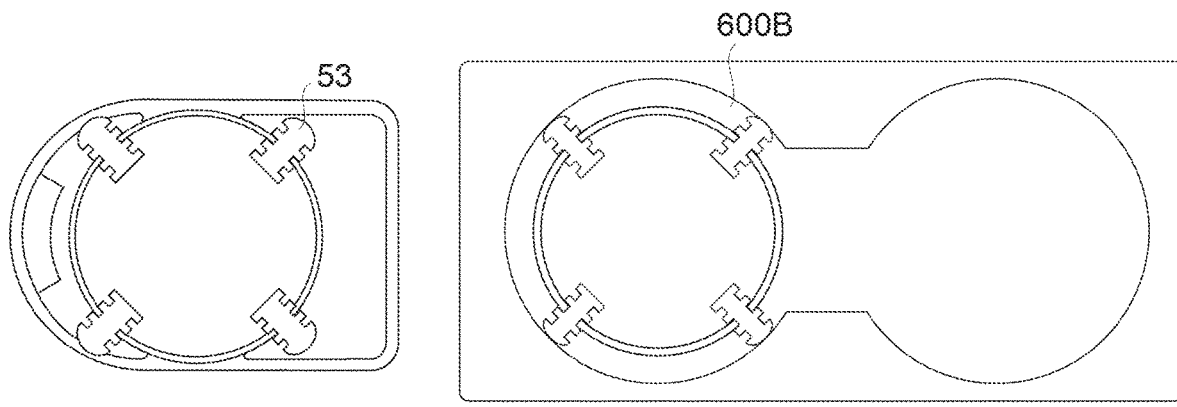
Figure 13C:
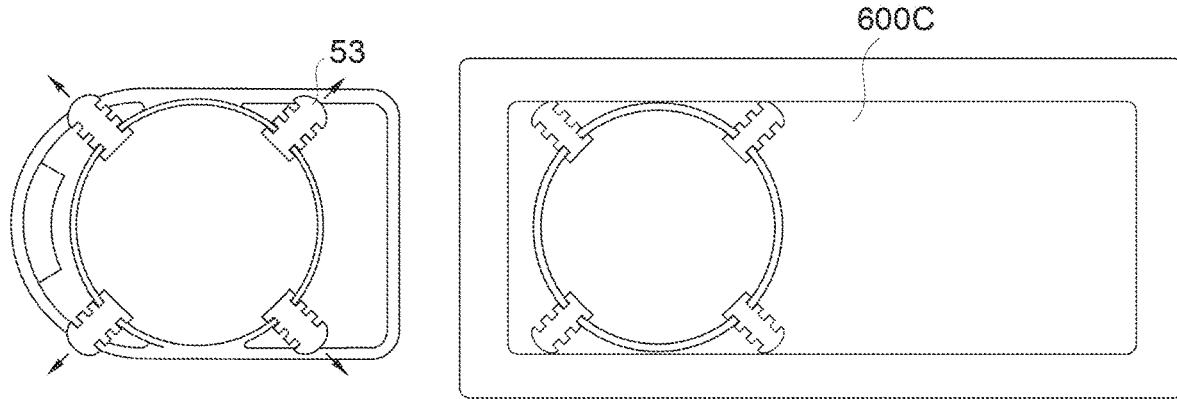

FIGS. 13A, 13B, and 13C show how silicone blocks 53 may be adjusted so that the cup 52 may be fit into cup holder of different diameters in a storage compartment of a vehicle.

As shown in FIG. 13A, the silicone blocks 53 are retreated almost entirely into the cup 52 so that the cup 52 may be received in a cup holder 600A of a smaller aperture. As shown in FIG. 13B, the silicone blocks 53 are extended outward so that the cup 52 may be reliably positioned in a cup holder of a greater aperture. As shown in FIG. 13C, the silicone blocks 53 are arranged so that they are entirely extended from the cup 52 so that the cup 52 may still be reliably positioned in a rectangular cup holder 600C.

Figure 14A:
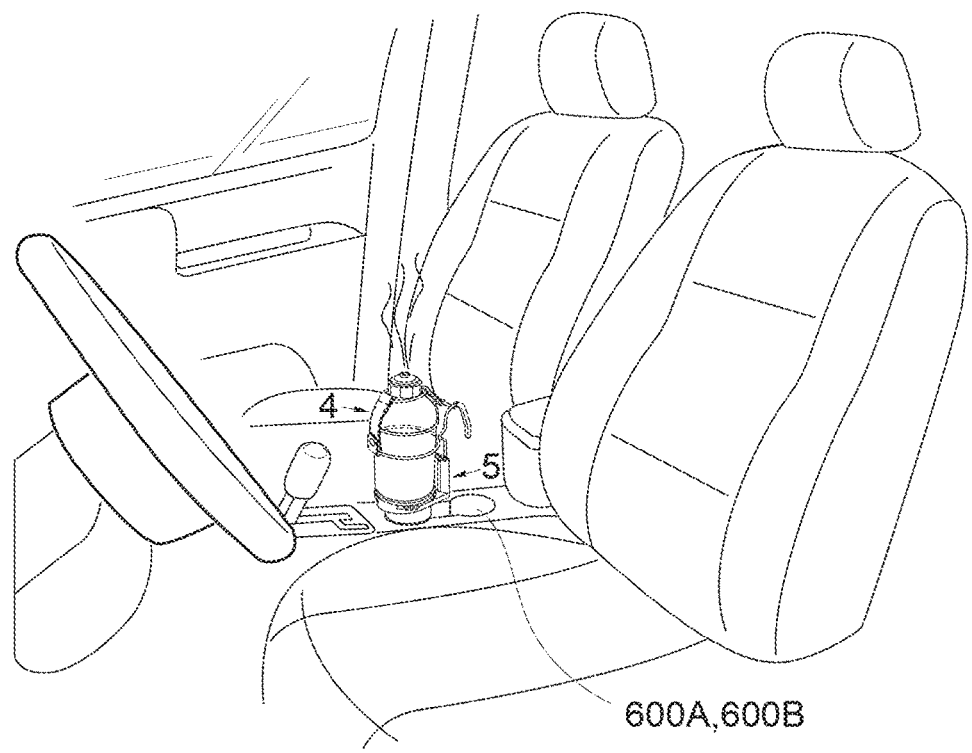
FIG. 14A shows a scenario of the holding device of FIG. 4 applied inside a vehicle to hold an air freshener in a cup holder.
Figure 14B:
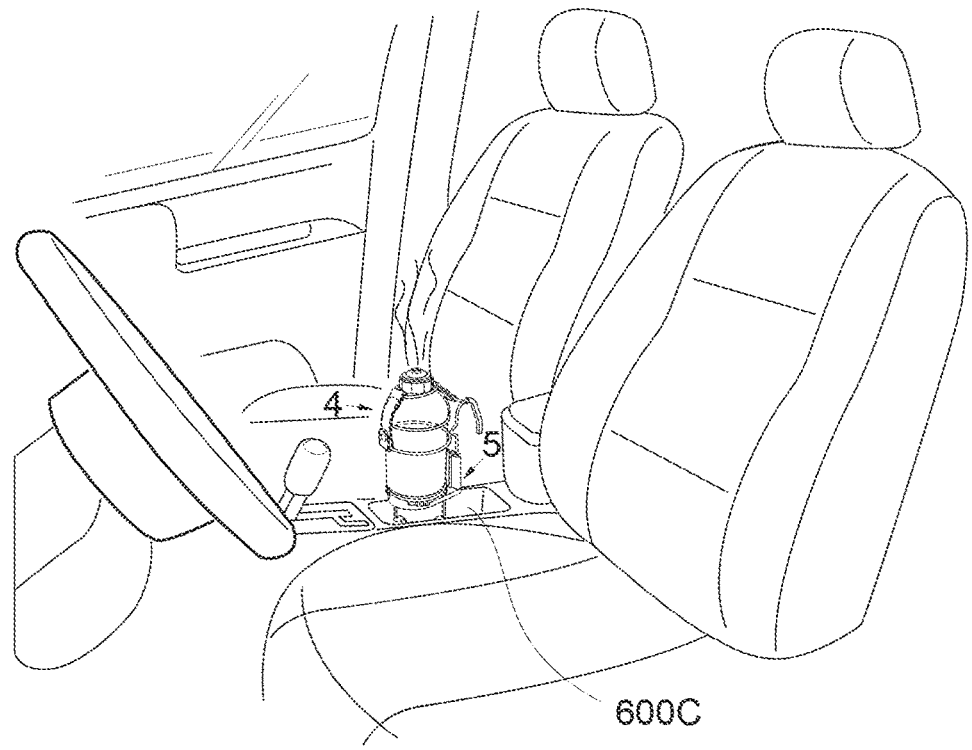
FIG. 14B shows another scenario of the holding device of FIG. 4 applied inside a vehicle to hold an air freshener in a cup holder.

As shown in FIGS. 14A and 14B, by appropriately adjusting the silicone blocks 53 around the cup 52, the air freshener 2 may be reliably positioned in round cup holders 600A and 600B of different apertures through the holding device of the present invention. The holding device may also be adjusted even for rectangular cup holder 600C.

Figure 15:
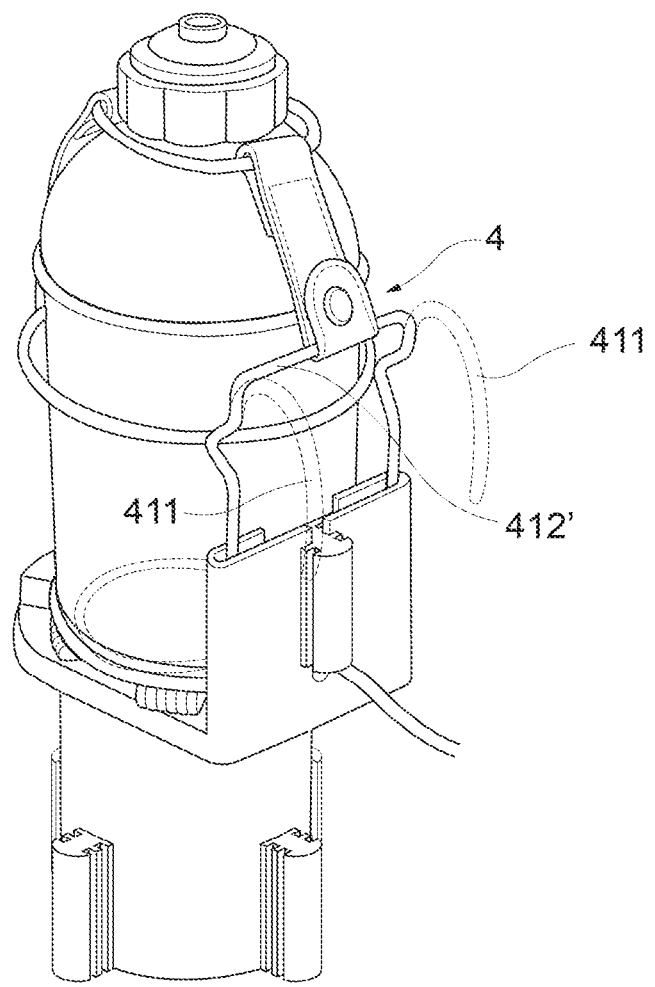
FIG. 15 is a perspective diagram showing a holding device according to another embodiment of the present invention.

As shown in FIG. 15, a holding device according to a second embodiment of the present invention omits the hooks 411 (shown by dashed lines) and the reinforcing beam 412' joins the top ends of the columns 413.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A holding device for an air freshener, comprising:
a hanging member comprising a rack and a belt, where the rack is formed by metallic wires and comprises two separate hooks arranged in parallel with a reinforcing beam in between, a back end of each hook is sleeved in a plastic cover, the hooks have their front ends extended downward into two columns, the two columns are bent perpendicularly forward and joined into a bottom ring, a top ring is perpendicularly welded to the columns above the bottom ring, the belt has a ring and two belt pieces, and each belt piece is extended from the ring and a buckle at an outer end of the belt piece;

a base member comprising a cup and an L-shaped seat with a planar element and a wall element, where the planar element has a round front edge with an arc-shaped block extended upward and a linear back edge joined to the wall element, the wall element comprises two wall pieces placed side by side with a ditch in between, the wall pieces have U-shaped ditches inside facing each other, the planar element has a central through opening, and the cup is joined to the planar element from below and exposed by the through opening;

wherein, the air freshener is adapted to be positioned on the hanging member, the air freshener and hanging member are adapted to be plugged into the base member; the columns are embedded into the U-shaped ditches; the arc-shaped block is adapted to be in front of and is adapted to confine the air freshener; a power cable of the air freshener is adapted to run through the ditch, a silicon block is inserted into the ditch and is adapted to confine the power cable.

2. The holding device according to claim 1, further comprising a plurality of silicone blocks, wherein a plurality of slots are configured around a lower portion of a circumference of the cup; each silicone block is plugged into a slot; and each silicone block has notches along two opposite sides so that the silicon block is extended for a different distance from the circumference as it is plugged into the slot.

3. A holding device for an air freshener, comprising:

a hanging member comprising a rack and a belt, where the rack is formed by metallic wires and comprises two columns arranged in parallel with a reinforcing beam in between, the columns are bent perpendicularly forward and joined into a bottom ring, a top ring is perpendicularly welded to the columns above the bottom ring, the belt has a ring and two belt pieces, and each belt piece is extended from the ring and a buckle at an outer end of the belt piece;

a base member comprising a cup and an L-shaped seat with a planar element and a wall element, where the planar element has a round front edge with an arc-shaped block extended upward and a linear back edge joined to the wall element, the wall element comprises two wall pieces placed side by side with a ditch in between, the wall pieces have U-shaped ditches inside facing each other, the planar element has a central through opening, and the cup is joined to the planar element from below and exposed by the through opening;

wherein, the air freshener is adapted to be positioned on the hanging member, the air freshener and hanging member are adapted to be plugged into the base member; the columns are embedded into the U-shaped ditches; the arc-shaped block is adapted to be in front of and is adapted to confine the air freshener; a power cable of the air freshener is adapted to run through the ditch, a silicon block is inserted into the ditch and is adapted to confine the power cable.

* * * * *